United States Patent [19]

Sakamoto et al.

[11] Patent Number: 5,372,940
[45] Date of Patent: Dec. 13, 1994

[54] D-PANTOLACTONE HYDROLASE AND PROCESS FOR THE PREPARATION THEREOF

[75] Inventors: Keiji Sakamoto, Takaoka; Hideaki Yamada, Kyoto; Sakayu Shimizu, Kyoto, all of Japan

[73] Assignee: Fuji Yakuhin Kogyo Kabushiki Kaisha, Toyama, Japan

[21] Appl. No.: 859,439

[22] PCT Filed: Oct. 4, 1991

[86] PCT No.: PCT/JP91/01351

§ 371 Date: Jun. 2, 1992

§ 102(e) Date: Jun. 2, 1992

[87] PCT Pub. No.: WO92/06182

PCT Pub. Date: Apr. 16, 1992

[30] Foreign Application Priority Data

Oct. 5, 1990 [JP] Japan ................... 2-266466

[51] Int. Cl.⁵ .................... C12P 17/02; C12N 9/14
[52] U.S. Cl. .................... 435/195; 435/123; 435/280; 435/256.5; 435/126
[58] Field of Search ........... 435/195, 196, 126, 280, 435/123, 256.5

[56] References Cited

U.S. PATENT DOCUMENTS 3,850,750  11/1974  Lanzioletta .................... 435/126
5,084,392   1/1992  Miyazawa et al. ............. 435/126

FOREIGN PATENT DOCUMENTS 0152895  9/1982  Japan .................... 435/126
0098695  6/1984  Japan .................... 435/126
0130192  7/1984  Japan .................... 435/126
1242586 10/1986  Japan .................... 435/126
2294092 12/1987  Japan .................... 435/126
4036276  2/1992  Japan .................... 435/126

OTHER PUBLICATIONS

Japanese Unexamined Patent Application Publication No. JP, A, 62-294092.
Japanese Unexamined Patent Application Publication No. JP, A, 57-1528-95.
Japanese Unexamined Patent Application Publication No. JP, B1 47-19745.
Japanese Unexamined Patent Application Publication No. JP, A,3-65198.
Derwent Biotechnology Abstract AN:. 90-10004.
Derwent Biotechnology Abstract AN: 88-04298.
Derwent Abstract AN: 85-287881.
Canadian Patent Application 2,037,043.
Takashi et al. (1989), Journal of Chromatography 474, pp. 405–410.

*Primary Examiner*—Douglas W. Robinson
*Assistant Examiner*—Jeffrey J. Sevigny
*Attorney, Agent, or Firm*—Birch, Stewart, Kolasch & Birch

[57] ABSTRACT

The invention is drawn to a new enzyme that selectively hydrolyzes D-pantolactone in D,L-pantolactone and has the following characteristics:

(a) action: acts on pantolactone to produce the corresponding acid;

(b) specificity for substrate: acts specifically on D-pantolactone but not on L-pantolactone;

(c) pH stability: stable at pH5–9;

(d) optimal pH: 7.0–7.5;

(e) optimal temperature: ca. 50° C.; and (f) effect of various metal ions or inhibitors: inhibited by $Cd^{2+}$, $Hg^{2+}$ or $Cu^{2+}$ EDTA, as well as a process for the preparation thereof. The enzyme is preferably produced by cultivating the microorganisms of the genera Fusarium, Cylindrocarpon, and Gibberella, and most preferably the microorganism *Fusarium oxysporum* IFO 5942.

10 Claims, 2 Drawing Sheets

D-PANTOLACTONE HYDROLASE AND PROCESS FOR THE PREPARATION THEREOF

FIELD OF INDUSTRIAL APPLICATION

D-pantolactone is known as an intermediate in the preparation of D-pantothenic acid and pantethine. Both are useful as vitamins of medical or physiological importance.

The present invention relates to a new enzyme useful for the optical resolution of D,L-pantolactone and a process for the preparation thereof.

BACKGROUND ART

D-pantolactone has heretofore been prepared through optical resolution of chemically synthesized D,L-pantolactone.

Such process, however, requires the use of costly resolving agents such as quinine or brucine, and suffers from the drawback that the recovery of D-pantolactone is not easy.

Processes of optical resolution of D,L-pantolactone by enzymatic asymmetric hydrolysis have also been known from Japanese published unexamined patent application No. 57-52895 (JP, A, 57-152895) and Japanese published unexamined patent application No. 62-294092 (JP, A, 62-294092). In these processes, the L-pantolactone in D,L-pantolactone is selectively subjected to asymmetric hydrolysis using microorganisms to afford D-pantolactone. These processes have the disadvantage that L-pantolactone, not being completely hydrolysable, does not yield D-pantolactone of high optical purity, and they are also of little significance as practical processes for the preparation of D-pantolactone due to the fact that both the substrate concentration and the reaction rate are low.

As a result of extensive research on the asymmetric hydrolysis of D,L-pantolactone, the present inventors have previously found that D-pantolactone can be obtained efficiently from D,L-pantolactone through selective asymmetric hydrolysis by certain microorganisms of the D-pantolactone only in D,L-pantolactone to form D-pantoic acid, followed by separation, and conversion into D-pantolactone of the D-pantoic acid (see Japanese patent application No. 1-200347).

Thus, the present inventors have succeeded in providing a process for the preparation of D-pantolactone, characterized in that the D-pantolactone in D,L-pantolactone is selectively subjected to asymmetric hydrolysis using a microorganism possessing lactone-hydrolyzing ability selected from microorganisms belonging to the genera Fusarium, Cylndrocarpon, Gibbrella, Aspergillus, Penicillium, Rhizopus, Volutella, Gliocladium, Eurotium, Nectria, Schizophyllum, Myrothecium, Neurospora, Acremonium, Tuberculina, Absidia, Sporothrix, Verticillium or Arthroderma, to form D-pantoic acid, which is then separated and converted into D-pantolactone. The invention has many advantages over the above-mentioned known processes of selective asymmetric hydrolysis of the L-pantolactone in D,L-pantolactone, for example in that considerably higher substrate concentrations may be used, that shorter reaction times may be employed, and that D-pantolactone of extremely high optical purity can be obtained.

DISCLOSURE OF THE INVENTION

Figure 1:
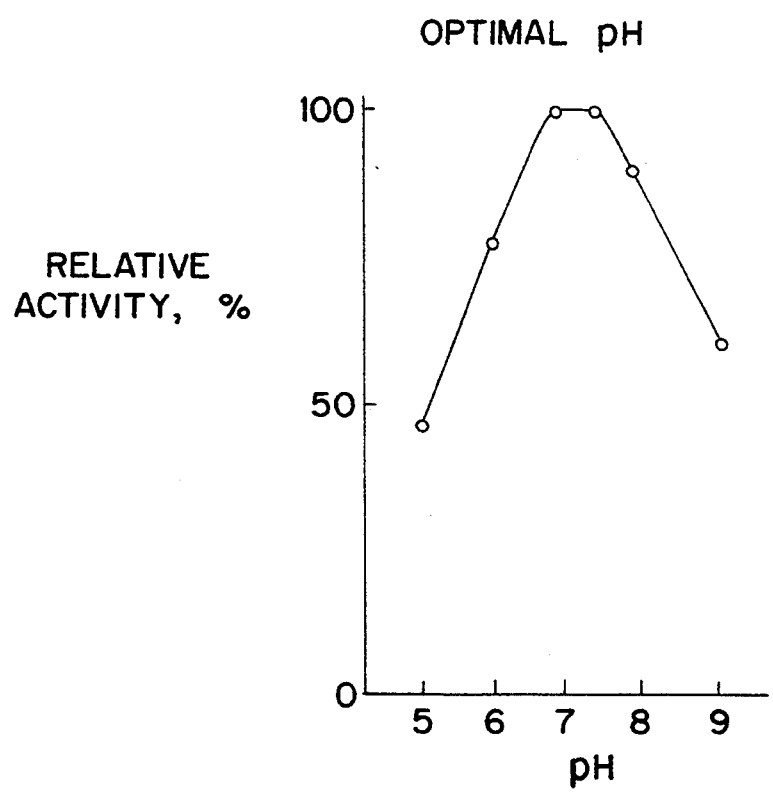
FIG. 1 shows the activity vs. pH relationship.
Figure 2:
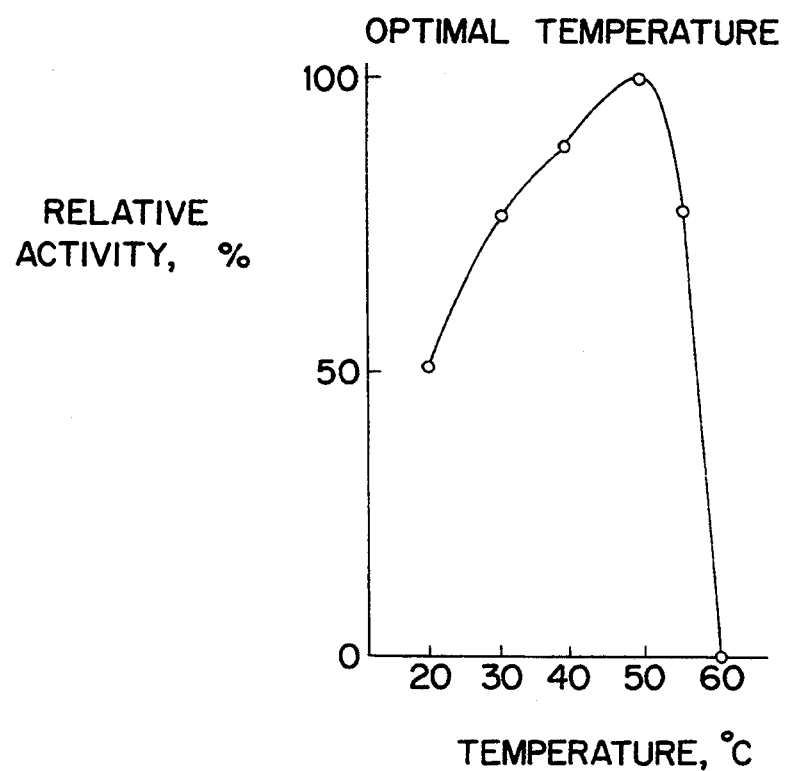
FIG. 2 shows the activity vs. temperature relationship.
Figure 3:
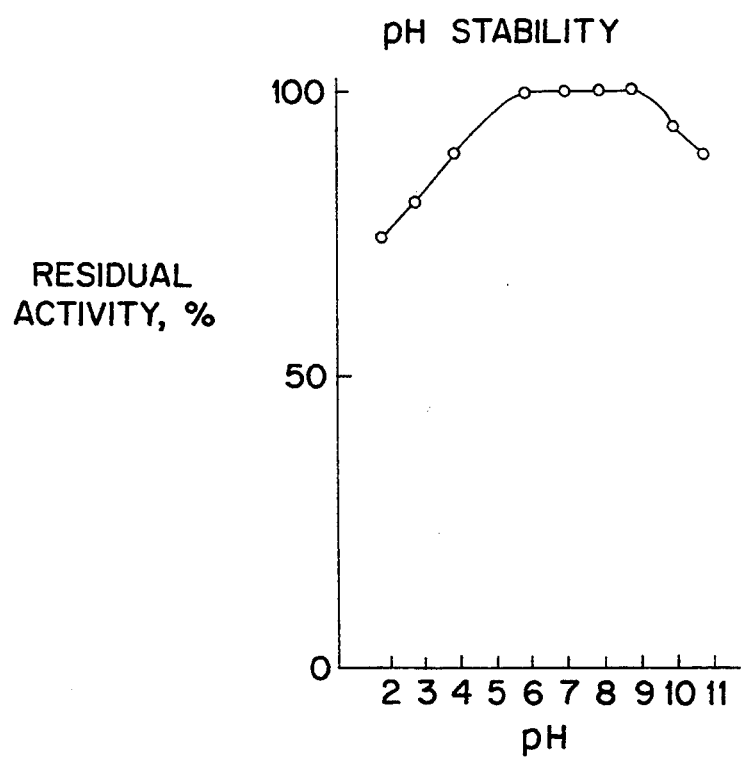
FIG. 3 shows the activity vs. pH relationship, as determined by treatment at 30 C for 60 minutes at different pH's.
Figure 4:
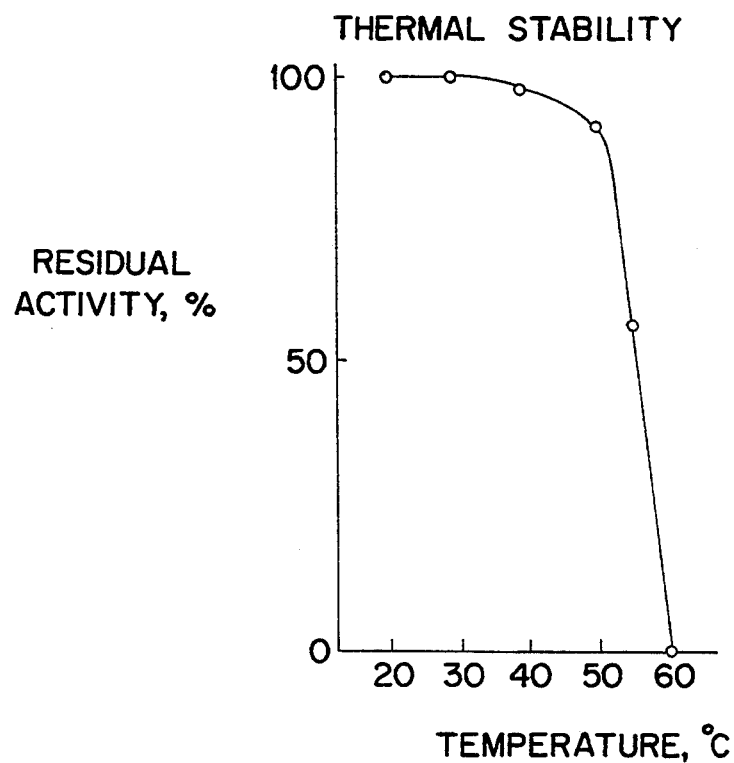
FIG. 4 shows the activity vs. temperature relationship, as determined by treatment at pH 7.0 for 60 minutes at different temperatures, of D-pantolactone hydrolase of the present invention.

The present inventors have now succeeded in obtaining a new enzyme capable of specifically hydrolyzing D-lactone from the specific microorganisms used in the present inventors' process mentioned above for the selective asymmetric hydrolysis of the D-pantolactone only in D,L-pantolactone. Thus, the present inventors have succeeded in obtaining a new D-pantolactone hydrolase from the culture broth to a microorganism with the ability of produce said new enzyme capable of specifically hydrolyzing D-pantolactone, selected from microorganisms belonging to the genera Fusarium, Cylindrocarpon, Gibberella, Asperillus, Penicillium, Rhizopus, Volutella, Gliocladium, Eurotium, Nectria, Schizophyllum, Myrothecium, Neurospora, Acremonium, Tuberculina, Absidia, Sporothrix, Verticillium or Arthroderma. Accordingly, the present invention provides such D-pantolactone hydrolase as well as a process for the preparation of said enzyme by means of microorganisms belonging to the genera mentioned above.

The following describes the present invention in, more detail.

The new enzyme according to the present invention is, in general, prepared in the following manner. A microorganism with D-pantolactone hydrolase-producing ability is selected from the microorganisms belonging to the genera Fusarium, Cylindrocarpon, Gibberella, Aspergillus, Penicillium, Rhizopus, Volutella, Gliocladium, Eurotium, Nectoria, Schizophyllum, Myrothecium, Neurospora, Acremonium, Tuberculina, Absidia, Sporothix, Verticillium or Arthroderma, and cultured said enzyme is obtained from the culture broth. Examples available to the public of such microorganisms are listed in Table 1.

TABLE 1

| Example No. | Identification of the Strain |
|---|---|
| 1 | *Fusarium oxysporum* IFO 5942 |
| 2 | *Cylindrocarpon tonkinense* IFO 30561 |
| 3 | *Gibberella fujikuroi* IFO 6349 |
| 4 | *Aspergillus awamori* IFO 4033 |
| 5 | *Penicillium chrysogenum* IFO 4626 |
| 6 | *Rhizopus oryzae* IFO 4706 |
| 7 | *Volutella buxi* IFO 6003 |
| 8 | *Gliocladium catenulatum* IFO 6121 |
| 9 | *Eurotium chevalieri* IFO 4334 |
| 10 | *Nectria elegans* IFO 7187 |

TABLE 1-continued

| Example No. | Identification of the Strain |
|---|---|
| 11 | *Schizophyllum commune* IFO 4928 |
| 12 | *Myrothecium roridum* IFO 9531 |
| 13 | *Neurospora crassa* IFO 6067 |
| 14 | *Acremonium fusidioides* IFO 6813 |
| 15 | *Tuberculina persicina* IFO 6464 |
| 16 | *Absidia lichtheimi* IFO 4009 |
| 17 | *Sporothrix schenckii* IFO 5983 |
| 18 | *Verticillium malthousei* IFO 6624 |
| 19 | *Arthroderma uncinatum* IFO 7865 |

N.B.: IFO No. stands for No. in the Catalog issued by ZAIDAN-HOJIN HAKKO-KENKYU-SHO (Institute for Fermentation Osaka, a juridical foundation)

In cultivating these microorganisms, any culture media, synthetic or natural, may be used insofar as they contain, as appropriate, carbon sources, nitrogen sources, inorganics or other nutrients.

There are used such media which contain saccharides such as glucose or sucrose, alcohols such as ethanol or glycerin, fatty acids such as oleic acid or stearic acid or esters thereof or oils such as rapeseed oil or soybean oil as carbon sources; ammonium sulfate, sodium nitrate, peptone, casamino acids, corn steep liquor, bran, yeast extract or the like as nitrogen sources; magnesium sulfate, sodium chloride, calcium carbonate, dipotassium monohydrogenphosphate, potassium dihydrogen phosphate or the like as inorganic salt sources; and malt extract, meat extract or the like as other nutrients.

The cultivation is carried out aerobically, normally for an incubation period of 1–7 days at a medium pH of 3–9 and an incubation temperature of 10°–50° C.

Carrying out of the cultivation in the manner as described above results n the production of large amounts of D-pantolactone hydrolase in the culture medium and/or the cells, which enzyme is then obtained in the following manner.

Since D-pantolactone hydrolase normally exists in cells, the procedure will now be described with particular reference to obtaining the enzyme from cells. After completion of the cultivation, the culture broth is filtered or centrifuged to obtain cells, which are washed well with water or buffer. The thus obtained cells are suspended in an appropriate volume of buffer and then disrupted. The disruption is carried out mechanically (as with a mortar, DYNO ®-MILL, French press, ultrasonic disruptor or the like).

The thus obtained disrupted suspension of cells is filtered or centrifuged to remove of solids to afford a cell-free extract, from which D-pantolactone hydrolase is obtained through conventional methods of enzyme isolation.

Thus, for example, there may be used combinations of such methods as ammonium sulfate precipitation, ion exchange chromatography, affinity chromatography, gel filtration and ultrafiltration.

To obtain enzyme which accumulates in the extracellular culture medium, the procedure as mentioned above may be followed, except in the operations of cell separation and cell disruption are omitted.

Thus, as will be mentioned in the working examples, the enzyme according to the present invention can be easily purified electrophoretically to homogeneity.

The enzyme according to the present invention may be characterized as follows:

(a) Action:
It acts on pantolactone to give the corresponding acid;

(b) specificity for substrate:
It acts specifically on D-pantolactone but not on L-pantolactone;

(c) pH stability:
It is stable at pH 5–9 (method of determination: 10 $\mu$l of 200 mM buffer of different pH values are added to 40 $\mu$l of enzyme solution and each mixture, after reaction at 30° C. for 30 minutes, is assayed for activity in accordance with the enzyme activity determination method as described below);

(d) optimal pH:
7.0–7.5 (Method of determination: 50 $\mu$l of enzyme solution is added to 200 $\mu$l of 2.5% D-pantolactone solution in 250 mM buffer of different pH values and each mixture, after reaction at 30° C. for 60 minutes, is assayed for activity);

(e) optimal temperature z
ca. 50° C. (Method of determination: After reaction at different temperatures for 60 minutes the activity is determined in accordance with the enzyme activity determination method);

(f) Effect of various metal ions or inhibitors:
It is inhibited by $Cd^{2+}$, $Hg^{2+}$, $Cu^{2+}$ or EDTA.

The following examples are given to illustrate the process for the preparation of the enzyme according to the present invention, but the invention is in no way restricted to these examples.

Example 1

*Fusarium oxysporum* (IFO 5942) was inoculated into each of thirty 2l shake flasks each containing 500 ml of culture medium containing 5% sucrose, 0.4% sodium nitrate, 0.2% dipotassium monohydrogenphosphate, 0.05% magnesium sulfate, 0.05% potassium chloride, 0.001% ferric sulfate and 0.002% zinc sulfate (pH 6.0), and subjected to shaking culture at 28° C. for 7 days. The combined culture broths were centrifuged to give 800 g of wet mass of cells. The cells were triturated by means of a DYNO ®-MILL with 2.5 l of 0.1 mM dithiothreitol-containing 20 mM Tris-HCl buffer (pH 7.4), and the mixture was centrifuged to give 2.3 l of cell-free extract. The specific activity of this cell-free extract and the optical purity of the D-pantoic acid formed were measured and the results are shown in Table 2 (see Example No. 1). Furthermore, 572 g of potassium chloride were added to, and dissolved in, this cell-free extract and the mixture was loaded on an Octyl sepharose CL4B column (3×28 cm) and eluted with 3M potassium chloride. 2.4 l of eluted active fractions were dialyzed against 0.1 mM dithiothreitol-containing 20 mM Tris-HCl buffer (pH 7.4). The resultant 2.9 l of enzyme solution were loaded on a DEAE Sephacel column (5.5×34 cm) and eluted with a linear gradient of 0 to 0.5M potassium chloride. 255 ml of eluted active fractions were loaded on a hydroxyapatite column (5×10 cm) and eluted with a linear gradient of 0 to 0.88M potassium phosphate buffer (pH 7.0). 425 ml of eluted active fractions were subjected to ultrafiltration using an Amicon YM 10, and 115 ml of the resultant enzyme concentrate were dialyzed against 0.1 mM dithiothreitol-containing 20 mM Tris-HCl buffer (pH 7.4). 190 ml of the enzyme solution were subjected to ultrafiltration using an Amicon YM 30 and 14.5 ml of the resultant enzyme solution was loaded on a sephacryl S-300 column (2.5×95 cm) and eluted with 0.2M potassium chloride. 44.5 ml of eluted active fractions were dialyzed against 0.1 mM dithiothreitol-containing 20 mM Tris-HCl buffer (pH 7.4), then loaded on a Q sepharose Fast Flow column (1.8×3 cm) and eluted with a linear gradient of 0 to 1M potassium chloride. 7 ml of eluted active fractions were dialyzed against 0.1 mM dithiothreitol-containing 20 mM Tris-HCl buffer (pH 7.4) to obtain 6.8 ml of purified enzyme solution. This purified enzyme solution showed only one band on electrophoresis and, after desalting by gel filtration and then freeze-drying, gave 5.1 mg of enzyme the form of a fine powder. The total activity was 1170 U, the specific activity was 232 U/mg and the yield was 38.8%.

Characteristics of the thus purified D-pantolactone hydrolase are described below.

(1) Method of enzyme activity determination:

In determining enzyme activity, the enzyme activity which hydrolyzes 1 μmol of D-pantolactone in one minute under the conditions specified below was taken as one unit (U).

50 μl of enzyme solution were added to 200 μl of 10% D-pantolactone solution in 0.5M PIPES buffer (pH 7.0). After reaction at 30° C. for 120 minutes, 250 μl of 2 mM EDTA solution in methanol were added to stop the reaction. The resultant reaction mixture was subjected to HPLC (Nucleosil $5C_{18}$ 4.6×150 mm; eluent 10% methanol; rate of flow 1 ml/min; detection wavelength 230 nm) to determine the % hydrolysis. For example, where the % hydrolysis is 1%, the enzyme activity/ml of enzyme solution corresponds to $1.6 \times 10^{-2}$ U/ml.

(2) specific activity of the purified enzyme: 232 U/mg of protein (3) Molecular weight:

125000 when measured by gel filtration, and 63000 when measured by SDS polyacrylamide gel electrophoresis. This suggests that the enzyme is a dimeric protein consisting of two subunits, each having a molecular weight of 63000.

(4) Isoelectric point: 4.7

(5) optimal pH: 7-7.5

(6) pH stability: stable at pH 5-9 (against treatment at 30° C. for 60 minutes)

(7) optimal temperature: ca. 50° C.

(8) Thermal stability: stable up to 50° C. (against treatment at pH 7.0 for 60 minutes)

(9) Specificity for substrate:

It acts specifically on D-pantolactone (Km: 82 mM, but not on L-pantolactone. It acts also on D-galactonolactone (Km: 3.6 mM), D-gulonolactone (Km: 29 mM) and L-mannonolactone (Km: 23 mM), wherein Km stands for Michaelis constant.

(10) Inhibitor:

The activity of the enzyme is inhibited by certain heavy metal ions. Representatives thereof are shown below. Values in parentheses are those for the activity of the respective metal ions at 2.5 mM concentration as measured with the activity value in the case of no addition of metal ions taken as 100. $Zn^{2+}$ (10), $Cd^{2+}$ (0), $Cu^{2+}$ (6), $Hg^{2+}$ (0). The enzyme is also inhibited completely by 5 mM EDTA.

Examples 2–19

The microorganisms described in Nos, 2–19 of Table 1 were used in place of *Fusirium oxysporum* (IFO 5942) used in Example 1. In accordance with the procedure described in Example 1, the respective microorganisms were cultivated and their respective culture broths were treated to give the corresponding cell-free extracts.

From each cell-free extract can be obtained, if necessary, the enzyme as pure product after purification.

Each cell-free extract was used to determine, in accordance with the enzyme activity determination method, the specific activity as well as the optical purity of the D-pantoic acid formed. The results are shown in Table 2 (see Example Nos. 2–19). The determination of the optical purity of the D-pantoic acid was carried out using HPLC (MCI GEL CRS 10 W 4.6×50 mm eluent 2 mM $CUSO_4$ solution in 10% methanol; rate of flow 0.8 ml/min detection wavelength 254 nm) (J. chromatogr., 474, 405 (1989)).

TABLE 2

| Example No. | Producing microorganisms | IFO No. | Specific activity (U/mg · protein) | Optical purity of D-pantoic acid (% e.e.) |
|---|---|---|---|---|
| 1 | Fusarium oxysporum | 5942 | 0.31 | 98.0 |
| 2 | Cylindrocarpon tonkinense | 30561 | 0.26 | 92.3 |
| 3 | Gibberella fujikuroi | 6349 | 0.22 | 91.4 |
| 4 | Aspergillus awamori | 4033 | 0.14 | 84.7 |
| 5 | Penicillium chrysogenum | 4626 | 0.28 | 83.1 |
| 6 | Rhizopus oryzae | 4706 | 0.09 | 80.5 |
| 7 | Volutella buxi | 6003 | 0.11 | 78.6 |
| 8 | Gliocladium catenulatum | 6121 | 0.03 | 74.2 |
| 9 | Eurotium chevalieri | 4334 | 0.25 | 71.1 |
| 10 | Nectria elegans | 7187 | 0.17 | 80.2 |
| 11 | Schizophyllum commune | 4928 | 0.16 | 81.5 |
| 12 | Myrothecium roridum | 9531 | 0.08 | 72.7 |
| 13 | Neurospora crassa | 6067 | 0.13 | 63.6 |
| 14 | Acremonium fusidioides | 6813 | 0.24 | 55.9 |
| 15 | Tuberculina persicina | 6464 | 0.09 | 43.8 |
| 16 | Absidia lichtheimi | 4009 | 0.27 | 36.7 |
| 17 | Sporothrix schenckii | 5983 | 0.17 | 33.4 |
| 18 | Verticillium malthousei | 6624 | 0.14 | 52.7 |
| 19 | Arthroderma uncinatum | 7865 | 0.21 | 38.9 |

We claim:

1. A purified D-pantolactone hydrolase possessing the following properties:
   (a) acts on pantolactone to produce the corresponding acid;
   (b) acts specifically on D-pantolactone but not on L-pantolactone;
   (c) molecular weight in the range from 63,000 to 125,000 as determined by sodium dodecyl sulfate polyacrylamide gel electrophoresis and gel filtration, respectively;
   (d) isoelectric point of 4.7;
   (e) stable in the pH range from 5 to 9;
   (f) pH optimum in the range from 7.0 to 7.5;
   (g) stable up to 50° C. at pH 7.0 for 60 minutes;
   (h) temperature optimum of about 50° C.; and (i) activity inhibited by Cd++, Hg++, Cu++, and EDTA.

2. A microbiological process for the preparation of D-pantolactone hydrolase according to claim 1, comprising cultivating a microorganism possessing the ability to produce D-pantolactone hydrolase, wherein said microorganism is a member selected from the group consisting of the genera (Fusarium, Cylindrocarpon, and Gibberella,) and recovering said D-pantolactone hydrolase from the culture broth or from disrupted cells of said microorganism.

3. A microbiological process for the preparation of D-pantolactone hydrolase according to claim 1, comprising cultivating a microorganism possessing the ability to produce D-pantolactone hydrolase, wherein said microorganism is a member selected from the group consisting of *Fusarium oxysporum* IFO 5942, *Cylindrocarpon tonkinense* IFO 30561, *Gibberella fujikuroi* IFO 6349, *Aspergillus awamori* IFO 4033, *Penicillium chrysogenum* IFO 4626, *Rhizopus oryzae* IFO 4706, *Volutella buxi* IFO 6003, *Gliocladium catenulatum* IFO 6121, *Eurotium chevalieri* IFO 4334, *Nectria elegans* IFO 7187, *Schizophyllum commune* IFO 4928, *Myrothecium roridum* IFO 9531, *Neurospora crassa* IFO 6067, *Acremonium fusidioides* IFO 6813, *Tuberculina persicina* IFO 6464, *Absidia lichtheimi* IFO 4009, *Sporothrix schenckii* IFO 5983, *Verticillium malthousei* IFO 6624, and *Arthroderma uncinatum* IFO 7865, and recovering said D-pantolactone hydrolase from the culture broth or from disrupted cells of said microorganism.

4. The process of claim 2 or 3, wherein said cultivating is carried out in a medium comprising a carbon source, a nitrogen source, and an inorganic salt.

5. The process of claim 4, wherein said carbon source is at least one member selected from the group consisting of a saccharide, an alcohol, a fatty acid, a fatty acid ester, and an oil.

6. The process of claim 5, wherein said saccharide is a member selected from the group consisting of glucose and sucrose, said alcohol is a member selected from the group consisting of ethanol and glycerin, said fatty acid is a member selected from the group consisting of oleic acid and stearic acid, said fatty acid ester is a member selected from the group consisting of an ester of oleic acid and an ester of stearic acid, and said oil is a member selected from the group consisting of rapeseed oil and soybean oil.

7. The process of claim 4, wherein said nitrogen source is at least one member selected from the group consisting of ammonium sulfate, sodium nitrate, peptone, casamino acids, corn steep liquor, bran, and yeast extract.

8. The process of claim 4, wherein said inorganic salt is at least one member selected from the group consisting of magnesium sulfate, sodium chloride, calcium carbonate, dipotassium monohydrogen-phosphate, and potassium dihydrogen phosphate.

9. The process of claim 4, wherein said medium further comprises malt extract or meat extract.

10. The process of claim 2 or 3, wherein said cultivating is carried out aerobically, for a period of 1 to 7 days, at a pH of 3 to 9, at a temperature of 10 to 50° C.

* * * * *